United States Patent [19]

Hirsch

[11] 4,161,507

[45] Jul. 17, 1979

[54] STABILIZED DIAGNOSTIC TEST STRIP FOR THE DETECTION OF UROBILINOGEN

[75] Inventor: Wolfgang Hirsch, Wunstorf, Fed. Rep. of Germany

[73] Assignee: Behringwerke Aktiengesellschaft, Marburg an der Lahn, Fed. Rep. of Germany

[21] Appl. No.: 917,585

[22] Filed: Jun. 21, 1978

[30] Foreign Application Priority Data

Jun. 23, 1977 [DE] Fed. Rep. of Germany ....... 2728236

[51] Int. Cl.$^2$ ...................... G01N 31/22; G01N 33/16
[52] U.S. Cl. .................................... 422/56; 23/230 B; 23/929
[58] Field of Search ..................... 23/230 B, 932, 929; 422/56

[56] References Cited

U.S. PATENT DOCUMENTS

| | | | |
|---|---|---|---|
| 3,446,599 | 5/1969 | Shand | 23/230 B |
| 3,850,576 | 11/1974 | Rittersdorf et al. | 23/230 B |
| 3,853,471 | 12/1974 | Rittersdorf et al. | 23/932 X |
| 3,853,476 | 12/1974 | Rittersdorf et al. | 23/230 B X |
| 3,989,462 | 11/1976 | Hirsch | 23/230 B X |

*Primary Examiner*—Arnold Turk
*Attorney, Agent, or Firm*—Curtis, Morris & Safford

[57] ABSTRACT

Test strips for detecting urobilinogen in biologic fluids, especially in urine, which show an improved stability to storage. The strips comprise a carrier containing a diazonium salt and as a stabilizer at least one phosphoric acid triamide of the formula

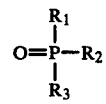

wherein $R_1$, $R_2$ and $R_3$ may be the same or different out of the group of amino-, mono- and dialkylamino-, mono- and diarylamino-, aralkylamino-, N-methylanilide-, N-piperidide- and N-morpholine-radicals.

4 Claims, No Drawings

STABILIZED DIAGNOSTIC TEST STRIP FOR THE DETECTION OF UROBILINOGEN

The present invention relates to a diagnostic composition for the detection of urobilinogen, preferably in biologic fluids, especially in urine, which contains a diazonium salt and is applied onto an absorbent carrier.

It is known to detect urobilinogen with a solution of dimethylaminobenzaldehyde in hydrochloric acid. This detection, known as Ehrlich's reaction, has achieved considerable importance in medical diagnosis in the course of time, although it is not very specific. The detection of urobilinogen in urine is regarded as being the standard method for the diagnosis of diseases of the liver and gall bladder. With the wide-spread application of rapidly acting diagnostic agents, test papers have been developed some time ago for the detection of urobilinogen based on Ehrlich's reaction (cf. German Offenlegungsschrift 15 98 140). These papers naturally possess the non-specificity of Ehrlich's test and suffer furthermore from the disadvantage that the color reaction develops very slowly.

In recent years test papers for the detection of urobilinogen in liquids have been described, the action of which is based on the coupling of a diazonium salt with urobilinogen. Among suitable reagents for this purpose there have been proposed aromatically substituted or annelated stable phenyl, pyrrole or pyrazole diazonium salts or substituted benzidine derivatives (cf. German Offenlegungsschrift No. 2,521,402 or U.S. Pat. No. 3,850,576). These test strips no longer possess the non-specificity of Ehrlich's test, however, the reaction zone is discolored during storage, as a consequence of which falsely positive results may be obtained or reading off of the reaction is rendered impossible.

The present invention was confronted with the problem of providing a stabilized diagnostic composition for the detection of urobilinogen, especially in urine, which should contain a diazonium salt applied onto an absorbent carrier and which should not discolor during storage.

It has now been found surprisingly that this problem can be solved by using a diagnostic composition which contains as stabilizer at least one phosphoric acid triamide of the formula I

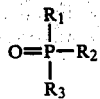

in which $R_1$, $R_2$ and $R_3$, which may be the same or different, are radicals selected from the group of amino-, mono- and dialkylamino-, mono- and diarylamino-, aralkylamino-, N-methylanilide-, N-piperidide- and N-morpholine.

The preferred compounds are phosphoric acid tris-n-methylanilide, phosphoric acid tripiperidide and phosphoric acid trimorpholide.

Phosphoric acid amides have been proposed for use in test strips (cf. German Offenlegungsschrift 2,235,127), where they are employed to stabilize a hydroperoxide. The mechanism of this stabilizing effect is not yet known. For this reason it was not to be expected at all that these phosphoric acid amides would be capable of avoiding a discoloration of an urobilinogen test paper during storage. Tests carried out for clearing up this stabilization effect showed that the fact that a discoloration does not occur cannot be attributed to a stabilization of the diazonium salt.

Thus a further advantage of the diagnostic compositions according to the invention, in addition to the advantages of customary test papers, namely specificity of the reaction and easy reading, resides in their improved storage stability.

For the preparation of the test papers, the phosphoric acid amides together with an acid and a diazonium compound, are applied onto an absorbent carrier, optionally with additives such as wetting agents or optical brighteners.

For preparing the test paper, an absorbent carrier, preferably paper or a polyester fleece, is impregnated with a solution of the above reagents in a mixture of an organic solvent miscible with water and subsequently, the impregnated carrier is dried at a temperature of from 0° to 80° C. in air in motion.

The diazonium compounds which are added to the impregnation solution in an amount of from 0.02 to 2 g, preferably 0.1 to 0.5 g/100 ml, may be prepared according to the methods commonly known in diazo chemistry or are produced in the impregnation solution from the corresponding aromatic amines according to the methods known in diazo chemistry.

Suitable solid acids, which are added to the impregnation solution in an amount of from 1 to 30 g, preferably of from 5 to 15 g/100 ml, include organic aromatic and aliphatic carboxylic or sulfonic acids alone or in admixture with other inorganic acids.

Appropriate stabilizers for diazonium salts, for example naphthalene-1,5-disulfonic acid disodium salt or sodium lauryl sulfate, are well known in diazo chemistry. They may be added in an amount of from 1 to 10 g, preferably 1 to 7 g/100 ml of the impregnation solution.

Wetting agents, for example dodecylbenzene-sulfonic acid or sodium lauryl sulfate may be added in an amount of from 0.1 to 5 g, preferably of from 0.5 to 1 g/100 ml of the impregnation solution. Optical brighteners which improved the reading, may be added in an amount of from 0.01 to 5 g, preferably of from 0.1 to 2 g/100 ml of the impregnation solution.

As solvents there may be used water in combination with an organic solvent miscible in water, preferably a lower alcohol, for example methanol, the ratio between water and solvent being not critical, but depending only on the solubility of the components.

Suitable absorbent carriers are filter papers, however fleeces made from polyamide or polyester or other acid-resistant plastics may also be used. The material of the absorbent carrier is not critical. Other materials which are capable of absorbing the impregnation solution may alternatively be used. The individual components of the formulations can also be applied successively onto the carrier, if the solubility or particular circumstances require this.

The following example illustrate the stabilized diagnostic composition according to the invention for the detection of urobilinogen in liquids, without limiting the subject of the invention.

EXAMPLE

Impregnation solution A:
20 g of meta-phosphoric acid
6 g of citric acid 1-hydrate
14 g of naphthalene-1,5-disulfonic acid disodium salt 180 ml of permutite water.

Two grams of each of the following compounds are dissolved in the solution:
(a) phosphoric acid trimorpholide,
(b) phosphoric acid tris-n-methylanilide,
(c) phosphoric acid tripiperidide.

Impregnation solution B:
375 mg of 4-fluoro-3-nitrobenzene-diazonium-trifluoromethylsulfonate,
50 ml of methanol.

Filter paper No. 2316 of the firm Schleicher and Schüll, is impregnated with a mixture of the solutions A and B and is subsequently dried in a drying cabinet at 40° C. Thereafter the test papers are stored for 10 days at 70° C. with the exclusion of humidity of the air. A test paper which has been prepared without the addition of phosphoric acid triamide exhibits a brownish coloration after this period of time. The paper containing phosphoric acid trimorpholide has colored white, the paper containing phosphoric acid tris-n-methylanilide has colored slightly brownish and the paper containing phosphoric acid tripiperidide has colored slightly greyish.

What is claimed is:

1. A stabilized diagnostic test strip for the detection of urobilinogen, preferably in biologic fluids, especially in urine, comprising an absorbent carrier containing a diazonium salt and an acid, and as a stabilizer at least one phosphoric acid triamide of the formula

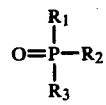

in which $R_1$, $R_2$ and $R_3$, which may be the same or different, are radicals selected from the group of amino-, mono- and dialkylamino-, mono- and diarylamino-, aralkylamino-, N-methylanilide-, N-piperidide- and N-morpholine.

2. Stabilized diagnostic test strip as claimed in claim 1, which contains as said stabilizer phosphoric acid tris-n-methyl-anilide.

3. Stabilized diagnostic test strip as claimed in claim 1, which contains as said stabilizer phosphoric acid tripiperidide.

4. Stabilized diagnostic test strip as claimed in claim 1, which contains as said stabilizer phosphoric acid trimorpholide.

* * * * *